United States Patent [19]

West et al.

[11] Patent Number: 5,157,180
[45] Date of Patent: Oct. 20, 1992

[54] ALKYLATION AND TRANSALKYLATION PROCESSES

[75] Inventors: Martin West, Huntington Beach; Suheil F. Abdo, Placentia, both of Calif.

[73] Assignee: Union Oil Company of California, Los Angeles, Calif.

[21] Appl. No.: 695,105

[22] Filed: May 3, 1991

Related U.S. Application Data

[62] Division of Ser. No. 358,432, May 26, 1989, Pat. No. 5,036,033.

[51] Int. Cl.$^5$ .................................................. C07C 2/66
[52] U.S. Cl. ..................... 585/313; 585/323; 585/446; 585/449; 585/467; 585/475; 585/481
[58] Field of Search ............... 585/449, 450, 453, 467, 585/312, 313, 323, 331, 475, 481; 208/46

[56] References Cited

U.S. PATENT DOCUMENTS

| | | | |
|---|---|---|---|
| 3,404,086 | 10/1968 | Plank et al. | 502/86 |
| 3,493,519 | 2/1970 | Kerr et al. | 502/86 |
| 3,541,174 | 11/1970 | Inoue et al. | |
| 3,631,120 | 12/1971 | Eberly, Jr. et al. | |
| 3,641,117 | 2/1972 | Eberly, Jr. et al. | |
| 3,701,814 | 10/1972 | Shilling | 585/467 |
| 3,929,672 | 12/1975 | Ward | |
| 4,169,111 | 9/1979 | Wight | |
| 4,185,040 | 1/1980 | Ward et al. | |
| 4,459,426 | 7/1984 | Inwood et al. | |
| 4,500,422 | 2/1985 | Miale et al. | 208/117 |
| 4,536,485 | 8/1985 | Topp-Jorgensen | 502/86 |
| 4,570,027 | 2/1986 | Boucher et al. | |
| 4,798,816 | 1/1989 | Ratcliffe et al. | |
| 4,837,398 | 6/1989 | Chang et al. | 502/62 |
| 4,863,885 | 9/1989 | Degnan, Jr. | 502/86 |
| 4,946,579 | 8/1990 | Occelli | 585/467 |
| 4,996,385 | 2/1991 | Cullo et al. | 585/467 |
| 5,036,033 | 7/1991 | West et al. | 502/64 |

FOREIGN PATENT DOCUMENTS 2310963 12/1976 France.
1506429 4/1978 United Kingdom.

Primary Examiner—Anthony McFarlane
Attorney, Agent, or Firm—Yale S. Finkle; Gregory F. Wirzbicki

[57] ABSTRACT

A process for producing an alkylated organic compound via alkylation and/or transalkylation in which an organic feedstock is contacted with an organic reactant in the presence of a catalyst under conditions such that components of the organic feedstock react with the organic reactant to form an alkylated compound. The catalyst comprises a molecular sieve having alkylation and/or transalkylation activity and contains, after calcination, between about 250 and 20,000 ppmw ammonium ions, calculated as $(NH_4)_2O$ on a volatiles-free basis. In two preferred embodiments of the invention, the catalyst is employed, respectively, in the alkylation zone of a process for producing cumene via the alkylation of benzene with propylene and in the alkylation zone of a process for producing ethylbenzene via the alkylation of benzene with ethylene.

31 Claims, 3 Drawing Sheets

ALKYLATION AND TRANSALKYLATION PROCESSES

CROSS REFERENCES TO RELATED APPLICATIONS

This application is a division of U.S. patent application Ser. No. 358,432, filed in the U.S. Patent and Trademark Office on May 26, 1989, now U.S. Pat. No. 5,036,033.

BACKGROUND OF THE INVENTION

This invention relates to alkylation and transalkylation processes and a catalyst for use therein. The invention is particularly concerned with a catalyst which, when used in alkylation and transalkylation processes, minimizes side reactions, such as cracking and cyclization, that lead to undesired by-products and therefore has an improved selectivity for the desired product.

In the past it has been common practice to alkylate aromatic molecules such as benzene, toluene and xylene with ethylene, propylene and other olefins using acidic homogeneous Friedel-Crafts type catalysts such as aluminum halides or heterogeneous acidic silica-alumina catalysts. Such processes have several disadvantages including corrosion problems caused by some of the catalysts and difficulty in controlling the product distribution obtained from the alkylation reactions. Often, the desired product is the monoalkylate rather than the di- or trialkylate. In an effort to avoid a large production of di- and trialkylate products and to extend catalyst life, it is conventional practice to use a large excess of the aromatic compound.

To avoid some of the problems associated with earlier commercial alkylation processes, solid zeolite-containing catalysts have been used in recent years to promote the alkylation of aromatic compounds with olefins and other alkylating agents, especially the alkylation of benzene with ethylene. Such zeolite-containing catalysts are normally prepared by combining a zeolite with a refractory oxide binder or precursor thereof, mulling and extruding the mixture, drying the extrudates and then calcining the dried extrudates at high temperatures to provide the extrudates with the strength required to withstand commercial operations. Naturally occurring and synthetic zeolites typically contain a relatively large concentration of sodium ions and are therefore not catalytically active. Thus, before a zeolite is mixed with the refractory oxide component or precursor thereof in the manufacturing of a zeolite-based catalyst, the zeolite is normally subjected to ion exchange, typically with ammonium ions, to reduce its sodium concentration as low as practically possible and increase its catalytic activity. However, since ammonia is known to poison the acid sites of the zeolite, it is common practice to carry out the calcination of the dried extrudates at such temperatures that substantially all of the ammonium ions in the catalyst are decomposed into hydrogen ions and ammonia which is driven out of the catalyst as a gas. Often, such catalysts will contain less than 50 ppmw ammonium ions, calculated as $(NH_4)_2O$ on a volatiles-free basis.

Normally, zeolite-based alkylation catalysts prepared as described above are used in fixed bed reactors through which the reactants are continuously passed. Although such fixed bed processes using zeolite-containing catalysts have advantages over earlier commercial processes, the selectivity for monoalkylation, especially when producing cumene by reacting propylene with benzene, has been observed in pilot plant studies to vary from one catalyst batch to another with some of the selectivities being so low that impurities appear in the product stream in concentrations large enough to dictate the use of additional equipment or process modifications to reduce the impurity level.

Accordingly, it is one of the objects of the present invention to provide a catalyst containing a zeolitic or nonzeolitic molecular sieve, and a method for preparing such a catalyst, that has high selectivities for the desired product when used to catalyze alkylation and transalkylation reactions, which selectivities do not substantially vary from one batch of catalyst to another. This and other objects of the invention will become more apparent in view of the following description of the invention.

SUMMARY OF THE INVENTION

In accordance with the invention, it has now been surprisingly found that the selectivity of catalysts comprising an inorganic refractory oxide component and a crystalline molecular sieve is sensitive to the ammonium ion concentration in the catalyst. It has been further found, contrary to what is commonly believed in the art, that it is most desirable to maintain a minimum concentration of ammonium ions in such catalysts in order to avoid the production of undesirable amounts of by-products during alkylation and transalkylation. It has been found that this minimum concentration is about 250 ppmw ammonium ions, calculated as $(NH_4)_2O$ on a volatiles-free basis, preferably about 500 ppmw, and can range to an upper limit of about 20,000 ppmw. Accordingly, the invention is directed to a catalyst composition of stable and high selectivity which, in its broadest embodiment, contains a molecular sieve and at least about 250 ppmw ammonium ions, calculated as $(NH_4)_2O$ on a volatiles-free basis. Preferably, the molecular sieve used in preparing the catalyst is a steam-stabilized, modified Y zeolite. The concentration of ammonium ions in the catalyst typically ranges between about 1000 and 18,000 ppmw, calculated as $(NH_4)_2O$ on a volatiles-free basis, preferably between about 2000 and about 15,000 ppmw, more preferably between about 3000 and about 10,000 ppmw, and most preferably between about 4000 and 8000 ppmw. All concentrations referred to herein as being calculated on a volatiles-free basis are calculated based on the weight of the catalyst after it has been heated in an oven at 1000° C. for 2 hours to drive off moisture and other volatiles.

The catalyst of the invention is typically prepared by exchanging a molecular sieve with ammonium ions, mixing the resultant ion-exchanged sieve with a porous, inorganic refractory oxide component or precursor thereof, extruding the resultant mixture to form extrudates, drying the extrudates and then calcining the dried extrudates under conditions to control the amount of ammonium ions that are decomposed into ammonia and hydrogen ions so that the ammonium ion concentration of the catalyst is above the minimum level of 250 ppmw. As used herein, "extruding" includes all forms of pelleting including tableting, extruding, prilling and the like. Alternatively, if it is desired to use the catalyst in a fluidized bed reactor, a slurry of the ammonium-exchanged molecular sieve and refractory oxide component can be prepared and subsequently spray-dried to produce particles which typically range between 40 and 80 microns in diameter and have the desired ammonium ion concentration.

Catalysts of the invention have been found to have consistently high selectivities for the desired alkylated products and are therefore useful in a variety of alkylation and transalkylation processes in which an organic feedstock is contacted with an organic reactant to form an alkylated organic compound in the presence of such catalysts. In one specific embodiment of the process of the invention, the catalyst of the invention is employed in the alkylation zone of a process for producing cumene (isopropylbenzene) via the alkylation of benzene with propylene and is also employed downstream in the process in a transalkylation zone wherein benzene is subjected to transalkylation by contacting it with diisopropylbenzene, an undesired by-product of the reaction between benzene and propylene, to produce additional quantities of cumene.

DETAILED DESCRIPTION OF THE INVENTION

Figure 1:
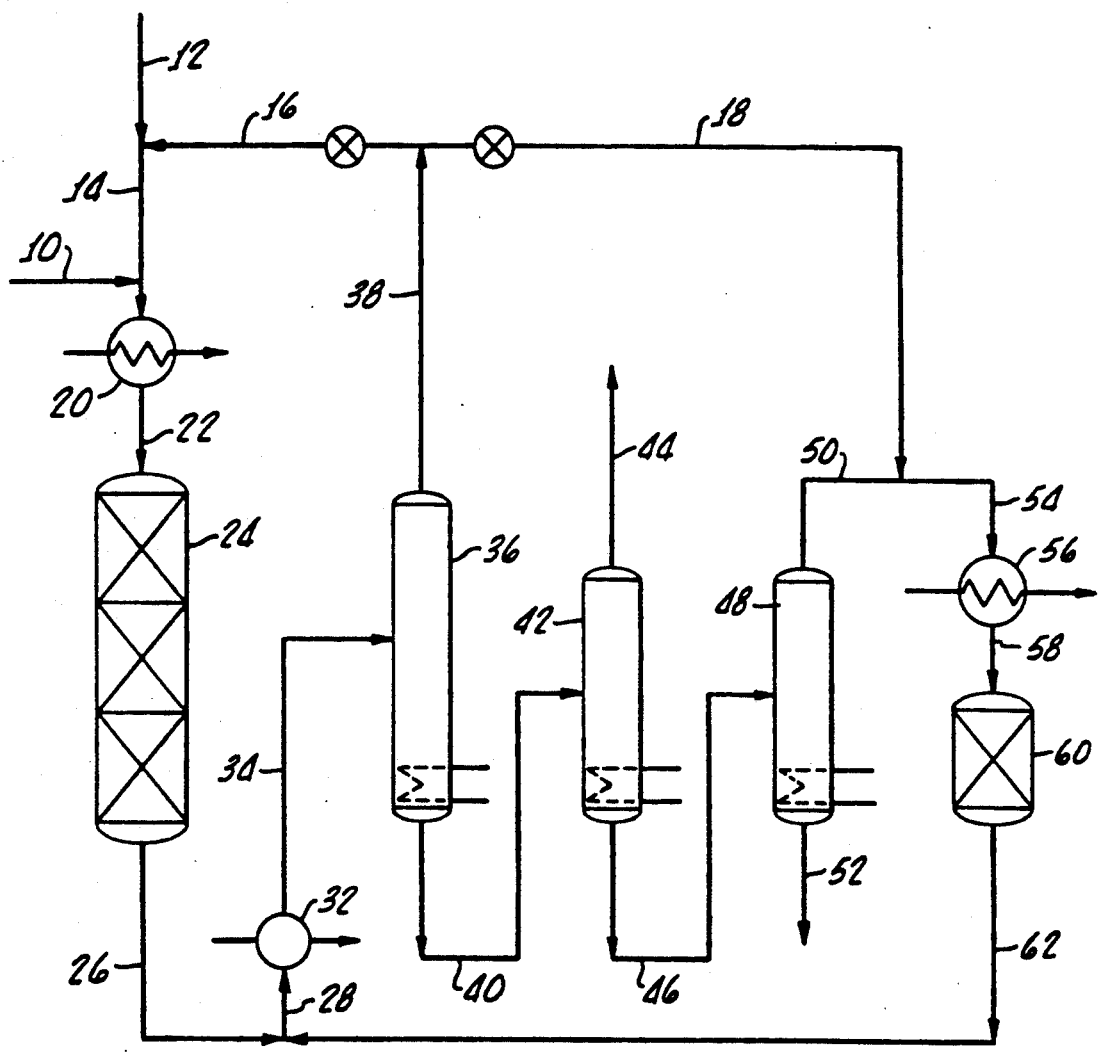
FIG. 1 in the drawing is a schematic flow diagram of a process for producing cumene or ethylbenzene utilizing both alkylation and transalkylation reactors containing the catalyst of the invention.

The molecular sieve-containing catalyst of the invention, which is typically free of hydrogenation metal components, will normally comprise a zeolitic or nonzeolitic molecular sieve composited with a porous, inorganic refractory oxide matrix or binder. The term "nonzeolitic" as used herein refers to molecular sieves whose frameworks are not formed of substantially only silica and alumina tetrahedra. The term "zeolitic" as used herein refers to molecular sieves whose frameworks are formed of substantially only silica and alumina tetrahedra such as the framework present in ZSM-5 type zeolites, Y zeolites, and X zeolites. Examples of nonzeolitic crystalline molecular sieves which may serve as the active alkylation or transalkylation component of the catalyst include silicoaluminophosphates, metalloaluminophosphates, ferrosilicates, chromosilicates, borosilicates, pillared clays, delaminated clays and crystalline silicas such as silicalite. Examples of zeolitic crystalline molecular sieves which may be used as the active alkylation or transalkylation component of the catalyst include those selected from the group of Y zeolites, fluorided Y zeolites, X zeolites, zeolite beta, zeolite L, zeolite omega and modifications of such zeolites. It is preferred that the molecular sieve used in the catalyst of the invention have a Constraint Index below about 1.0 and pores defined by 12-membered rings of oxygen atoms.

The preferred molecular sieves for use in the catalyst of the invention are Y zeolites and modified Y zeolites. U.S. Pat. No. 3,130,007, the disclosure of which is hereby incorporated by reference in its entirety, describes Y-type zeolites having an overall silica-to-alumina mole ratio between about 3.0 and about 6.0, with a typical Y zeolite having an overall silica-to-alumina mole ratio of about 5.0.

The modified Y zeolites suitable for use in preparing the catalyst of the invention are generally derived from Y zeolites by treatment which results in a significant modification of the Y zeolite framework structure, usually an increase in the framework silica-to-alumina mole ratio to a value typically above 6.0. It will be understood, however, that, in converting a Y zeolite starting material to a modified Y zeolite useful in the present invention, the resulting modified Y zeolite may not have exactly the same X-ray powder diffraction pattern for Y zeolites as is disclosed in U.S. Pat. No. 3,130,007. The d-spacings may be shifted somewhat due to a shrinkage in the unit cell size caused by an increase in the framework silica-to-alumina mole ratio. The essential crystal structure of the Y zeolite will, however, be retained so that the essential X-ray powder diffraction pattern of the modified zeolite used in the catalyst will be consistent with that of either Y zeolite itself or a Y zeolite of reduced unit cell size. Examples of modified Y zeolites that can be used in preparing the catalyst of the invention include ultrastable Y zeolites, steam-stabilized Y zeolites and dealuminated Y zeolites.

Steam-stabilized Y zeolites are Y zeolites which have been hydrothermally treated to increase the framework silica-to-alumina mole ratio but not the overall silica-to-alumina mole ratio of the zeolite. Steam stabilization normally involves calcination of the ammonium or hydrogen form of the Y zeolite starting material at relatively high temperatures, typically above about 900° F., in the presence of steam. This treatment results in the expulsion of tetrahedral aluminum from framework into nonframework positions, but normally does not remove the aluminum from the zeolite and therefore does not increase the overall silica-to-alumina mole ratio of the starting Y zeolite.

A preferred steam-stabilized Y zeolite for use as the starting molecular sieve in preparing the catalyst of the invention is one produced by (1) ammonium exchanging a Y zeolite to a sodium content between about 0.6 and 5 weight per cent, calculated as Na$_2$O, (2) calcining the ammonium-exchanged zeolite at a temperature between about 600° F. and 1650° F. in the presence of steam at a water vapor partial pressure of at least 0.2 p.s.i.a., preferably above about 2.0 p.s.i.a., and most preferably between about 5.0 and 15 p.s.i.a., to reduce the unit cell size of the ammonium-exchanged zeolite to a value in the range between about 24.35 and about 24.65 Angstroms, preferably between about 24.40 and 24.64 Angstroms, and then (3) ammonium exchanging the steam-calcined zeolite to replace at least 25 percent of the residual sodium ions and obtain a zeolite product containing less than about 1.0 weight percent sodium, preferably less than about 0.6 weight percent sodium, and most preferably below about 0.2 weight percent sodium, calculated as Na$_2$O. Such a Y zeolite is highly stable and maintains a high activity. The zeolite is described in detail in U.S. Pat. No. 3,929,672, the disclosure of which is hereby incorporated by reference in its entirety. The same or similar zeolites are now sold by UOP (formerly the Linde Division of Union Carbide Corporation) as LZY-82 zeolite, by PQ Corporation as CP300-56 and by Conteka-BV as CBV-530 and CBV- 531. The ammonium exchange steps described above may be facilitated by adding an acid to the ammonium solutions utilized in carrying out the exchanges.

The dealuminated Y zeolites that can be used as the starting molecular sieve for preparing the catalyst are Y zeolites which have been chemically treated with acids, salts, or chelating agents to increase the overall silica-to-alumina mole ratio. A preferred group of dealuminated zeolites is prepared by dealuminating a Y zeolite having an overall silica-to-alumina mole ratio below about 6.0 and is described in detail in U.S. Pat. Nos. 4,503,023 and 4,711,720, the disclosures of which patents are hereby incorporated by reference in their entireties. A preferred member of this group is known as LZ-210, a zeolitic alumino-silicate molecular sieve available from the Linde Division of the Union Carbide Corporation. LZ-210 zeolites and other zeolites of this group are conveniently prepared from a Y zeolite starting material in overall silica-to-alumina mole ratios between about 6.0 and about 20, although higher ratios are possible. Preferred LZ-210 zeolites have an overall silica-to-alumina mole ratio of about 6.1 to about 16. Typically, the unit cell size is at or below 24.65 Angstroms and will normally range between about 24.40 and about 24.60 Angstroms. LZ-210 zeolites having an overall silica-to-alumina mole ratio below 20 generally have a sorptive capacity for water vapor of at least 20 weight percent based on the anhydrous weight of the zeolite at 25° C. and 4.6 millimeters mercury water vapor partial pressure. Normally, the oxygen sorptive capacity at 100 millimeters mercury and −183° C. will be at least 25 weight percent. In general, LZ-210 zeolites are prepared by treating Y zeolites with an aqueous solution of a fluorosilicate salt, preferably a solution of ammonium hexafluorosilicate.

Before the molecular sieve to be utilized in the catalyst of the invention is combined with the porous, inorganic refractory oxide which will serve as the binder or matrix for the sieve, it will normally be catalytically active for alkylation and transalkylation reactions and contain ammonium ions. The activity of the molecular sieve is typically dependent on the amount of alkali metals associated with the acid sites of the sieve. Some of the molecular sieves that are suitable for use in the catalyst, such as the steam-stabilized Y zeolite described above, will already contain ammonium ions and have such a low concentration of sodium or other alkali metal cations that they will possess the requisite activity and can be combined directly with the refractory oxide component. If, however, the molecular sieve contains a high concentration of sodium or other alkali metal cations, it is normally desirable to exchange the sieve with ammonium ions to lower the alkali metal content and provide the sieve with ammonium ions.

The ammonium ion exchange is carried out by mixing the molecular sieve with an aqueous solution containing a dissolved ammonium salt, such as ammonium nitrate, ammonium sulfate, ammonium chloride and the like. The resulting slurry is stirred for between about 1 and about 5 hours at temperatures above ambient but less than 100° C. If sodium levels below 0.50 weight percent are desired, the ion exchange procedure will normally have to be repeated at least once. Typically, the ion exchange procedure will be repeated at least twice and occasionally several times to reduce the sodium or other alkali metal content preferably to below 0.2 weight percent, calculated as $Na_2O$.

The molecular sieve possessing alkylation and/or transalkylation activity is combined with one or more inorganic refractory oxide components, or precursors thereof, such as alumina, silica, titania, magnesia, zirconia, beryllia, a naturally occurring clay, such as kaolin, hectorite, sepiolite, attapulgite, montmorillonite or beidellite, silica-alumina, silica-magnesia, silica-titania, mixtures thereof and other such combinations and the like. Examples of precursors that may be used include peptized alumina, alumina gel, hydrated alumina, silica-alumina hydrogel and silica sols. The inorganic refractory oxide components or precursors thereof, which serve as a matrix for the molecular sieve, are typically amorphous and are usually mixed or comulled with the molecular sieve in amounts such that the final dry catalyst mixture will comprise (1) between about 50 and about 95 weight percent molecular sieve, preferably between about 70 and 95 weight percent, and (2) between about 5 and 50 weight percent of one or more inorganic refractory oxides, preferably between about 5 and 30 weight percent.

The desired inorganic refractory oxide component(s) or precursor(s) thereof is typically mulled, normally in the form of a powder, with the ammonium-exchanged molecular sieve particles. After mulling, the mixture is extruded through a die having openings of a cross sectional size and shape desired in the final catalyst particles. The catalyst may be made in any shape extrudates including, among others, extrudates having the cross section of a circle or a three-leaf clover similar to the shape shown in FIGS. 8 and 8A of U.S. Pat. No. 4,028,227, the disclosure of which is hereby incorporated by reference in its entirety. Normally, the length of the catalyst particles ranges between about 0.10 and 0.50 inch and the diameter between about 0.03 and 0.08 inch. The preferred sizes of the catalyst particles are described in detail in U.S. Pat. No. 4,185,040, the disclosure of which is hereby incorporated by reference in its entirety. After the extruded catalyst has been broken into particles of the desired length, the catalyst particles are dried and subjected to calcination at an elevated temperature, normally between about 600° F. and about 1600° F., preferably between about 700° F. and about 1200° F., to produce a catalyst of high crushing strength.

It has typically been the practice in the art of making molecular sieve-containing catalysts of any type to carry out the final calcination step at temperatures that are sufficiently high to not only provide the high crushing strength required of the catalyst but also to decompose substantially all of the ammonium ions in the molecular sieve into ammonia and hydrogen ions, thereby activating the catalyst by removing ammonia which neutralizes the active acid sites in the molecular sieve. It has now been surprisingly found that the selectivity of alkylation and transalkylation catalysts prepared as described above is substantially decreased if most or all of the ammonium ions are decomposed during calcination. If the catalyst does not contain sufficient ammonium ions, the selectivity of the catalyst for monoalkylation, particularly for the alkylation of benzene with propylene to produce cumene and the transalkylation of benzene with diisopropylbenzene to produce cumene, will be decreased to such an extent that deleterious amounts of undesirable by-products will be present in the desired product. It has been found that for the alkylation catalyst to have optimum selectivity for the desired monoalkylate, the ammonium ion concentration in the catalyst must be above about 250 ppmw, calculated as $(NH_4)_2O$ on a volatiles-free basis.

In view of the above and in accordance with the invention, the calcination of the extruded catalyst particles is carried under time and temperature conditions sufficient to leave more than 250 ppmw ammonium ions, calculated as $(NH_4)_2O$ on a volatiles-free basis, in the catalyst. Typically, the calcination is carried out such that the calcined catalyst particles will contain greater than about 1000 ppmw ammonium ions, calculated as $(NH_4)_2O$ on a volatiles-free basis, preferably more than about 2000 ppmw, more preferably greater than about 3000 ppmw, and most preferably greater than about 4000 ppmw. Since ammonia neutralizes acid sites of the active molecular sieve, too high a concentration in the form of ammonium ions will result in decreasing the activity of the alkylation catalyst. Thus, it is normally not desirable to leave more than about 20,000 ppmw ammonium ions, calculated as $(NH_4)_2O$ on a volatiles-free basis, in the catalyst. Although such a relatively high concentration of ammonium ions will perhaps have a beneficial effect on selectivity, it most likely will have a deleterious effect on catalyst activity. Thus, the ammonium ion concentration of the catalyst must be selected so that there is a balance between selectivity and activity. Typically, the concentration of ammonium ions in the catalyst will range between about 2000 and about 15,000 ppmw ammonium ions, calculated as $(NH_4)_2O$ on a volatiles-free basis, preferably between about 3000 and about 10,000 ppmw, and most preferably between about 4000 and about 8000 ppmw.

As mentioned previously, the discovery that the ammonium ion concentration of a molecular sieve-based alkylation or transalkylation catalyst beneficially affects the selectivity of the catalyst is quite surprising in light of the conventional practice of decomposing substantially all of the ammonium ions during calcination in order to obtain optimum catalytic performance. Although the invention is not limited to any theory of operation, it is believed that this surprising phenomenon is due to the fact that alkylation reactions require weaker acid sites than cracking reactions and that undesirable by-products result from cracking larger molecules during alkylation. It is therefore believed that the selectivity of an alkylation or transalkylation catalyst is greatly improved by preferentially blocking highly acidic sites in the active molecular sieve component of the catalyst with ammonium ions.

Catalysts prepared as described above are useful in a wide variety of alkylation and transalkylation processes in which an alkylated organic compound is produced by contacting an organic feedstock with an organic reactant in the presence of the catalyst. Alkylation can be broadly defined as the addition or insertion of an alkyl group into a molecule. Thus, alkylation reactions are diverse in nature. In transalkylation reactions, which are closely related to alkylation reactions, an alkyl group moves from one molecule to another. The catalyst of the invention is effective in catalyzing both alkylation and transalkylation reactions with consistently high selectivity. In addition, the catalyst of the invention can be used to catalyze other acid catalyzed chemical conversion reactions such as isomerization and disproportionation reactions, particularly isomerization and disproportionation reactions involving aromatic and aliphatic compounds.

In general, the catalyst of the invention can be used to catalyze the alkylation of saturated and unsaturated, branched and straight chain, aliphatic compounds, monocyclic and polycyclic aromatic compounds and substituted derivatives of such monocyclic and polycyclic compounds, and cycloaliphatic compounds. The alkylating agent used may be any compound capable of reacting with the compound to be alkylated. Typical alkylating agents include alkenes or olefins, alcohols such as methanol, alkylhalides, esters, ethers, aldehydes, ketones, amines, and thiocyanates. The catalyst of the invention can also be used in any transalkylation process in which a polyalkylated organic compound is converted into a lesser alkylated or nonalkylated organic compound by transferring one or more alkyl groups from the polyalkylated compound to a similar compound containing fewer alkyl groups.

Although the catalyst of the invention can be used in any transalkylation or alkylation process, its preferable uses are in processes for the alkylation of aromatic hydrocarbons with $C_2$-$C_4$ olefins to produce monoalkyl aromatic compounds and in the transalkylation of aromatic compounds to produce monoalkyl aromatic compounds. Normally, the alkylating agent used in such alkylation processes will be ethylene, propylene, isobutene or n-butene. Usually a monoalkylated product is desired, but polyalkylated products can also be produced by, for instance, using toluene as the aromatic compound and ethylene as the alkylating agent.

The catalyst of the invention is preferably used in alkylation and transalkylation reactions to make cumene from benzene and propylene and to make ethylbenzene from benzene and ethylene. Cumene is commonly used as an intermediate to produce phenol while ethylbenzene is primarily used as an intermediate in producing styrene. FIG. 1 in the drawing illustrates a specific embodiment of the process of the invention in which the catalyst of the invention is utilized both as an alkylation and a transalkylation catalyst. This embodiment of the invention can be used to produce either cumene (isopropylbenzene) or ethylbenzene depending on whether the alkylating agent utilized is propylene or ethylene. When the process is utilized to produce cumene, propylene is passed through line 10 into line 14 where it is mixed with makeup benzene introduced into line 14 through line 12 and recycled benzene introduced into line 14 through line 16. The source of recycled benzene will be described in more detail hereinafter. The resultant mixture of propylene, makeup benzene and recycled benzene is passed through line 14 into preheater 20 and then through line 22 into adiabatic alkylation reactor 24.

The alkylation reactor may contain one or more beds of the catalyst of the invention. In the upper portion of the catalyst bed in the alkylation reactor, propylene reacts with benzene to produce cumene and polyalkylated aromatic compounds such as di- and triisopropylbenzenes. In the lower part of the reactor, these polyalkylated benzenes undergo transalkylation by reacting with benzene to form additional cumene. The temperature in preheater 20 is controlled, depending upon the feed composition, to yield the desired maximum temperature in the alkylation reactor. Typically, the temperature in the alkylation reactor will be between about 200° F. and 900° F., preferably between about 300° F. and 600° F., and is sufficiently low that ammonium ions in the catalyst are not decomposed and the formation of xylene is minimized. The pressure utilized in the reactor will range between about 150 p.s.i.g. and 2000 p.s.i.g., preferably between about 400 p.s.i.g. and 1500 p.s.i.g. The weight hourly space velocity typically ranges between about 2 and 2000 reciprocal hours, preferably between about 4 and 100 reciprocal hours. The mole ratio of benzene to propylene used typically ranges between about 1.0 and 100, preferably between about 4 and 40. The conditions of temperature and pressure are preferably correlated so that a liquid phase is present in the reactor. An excess of benzene is utilized in order to minimize the formation of polymers of the alkylating agent and undesired polyalkylated compounds.

The effluent from reactor 24 will contain, among other compounds, cumene, unreacted benzene, diisopropylbenzene, triisopropylbenzene, n-propylbenzene, ethylbenzene and other aromatic compounds. This mixture is withdrawn from alkylation reactor 24 through line 26, depressured and passed into line 28 where it is mixed with a recycle stream containing cumene which is introduced into line 28 through line 62. The mixture in line 28 is then passed into condenser 32 where the mixture is cooled to distillation temperature. The cooled mixture is then passed through line 34 into distillation column 36 where unreacted benzene is taken overhead via line 38 and recycled in part to alkylation reactor 24 via lines 16, 14 and 22.

The bottoms product from distillation column 36, which comprises cumene, diisopropylbenzene and other benzene-derived impurities, is passed through line 40 to distillation column 42 from which the desired product cumene is recovered overhead through line 44. The bottoms product from column 42 is passed through line 46 into distillation column 48 wherein diisopropylbenzene is removed overhead through line 50 while a bottoms fraction comprising high boiling undesirable by-products is removed from the distillation column through line 52 to prevent build up of such compounds in the system.

The overhead stream from distillation column 48 is passed through line 50, mixed with benzene withdrawn overhead of distillation column 36 through lines 38 and 18, and passed through line 54 to preheater 56 and then through line 58 into transalkylation reactor 60. Here the mixture of diisopropylbenzene and benzene is passed over the catalyst of the invention under conditions such that transalkylation occurs, i.e., propyl groups are equilibrated from the diisopropylbenzene to the benzene to form additional isopropylbenzene or cumene, which is the desired product from this embodiment of the invention. The transalkylation reactor is normally operated at a temperature between about 250° F. and about 550° F., preferably between about 275° F. to about 500° F., such that at least some of the reactants are present in the liquid phase. The pressure in the transalkylation reactor will typically range between about 50 p.s.i.g. and about 2000 p.s.i.g., preferably between about 100 p.s.i.g. and 700 p.s.i.g. The weight hourly space velocity will normally range from about 0.5 to 50 reciprocal hours, preferably between about 1 and 15 reciprocal hours. The mole ratio of benzene to diisopropylbenzene introduced into the reactor will generally range between about 1 and about 50, preferably between about 5 and about 40.

The effluent from transalkylation reactor 60 is withdrawn through line 62 and passed to line 28 where it is mixed with the bottoms from alkylation reactor 24 and subsequently passed through distillation column 36 to distillation column 42 for recovery of the additional cumene produced in the transalkylation reactor.

Pilot plant tests using different batches of alkylation and transalkylation catalysts containing a steam-stabilized Y zeolite as the active alkylation component indicate that the levels of the contaminant ethylbenzene in the product cumene that would be recovered overhead of distillation column 42 through line 44 in FIG. 1 will vary and that some catalyst batches will yield levels of ethylbenzene that are unacceptably high, thereby making it necessary to use additional equipment or process modifications to reduce ethylbenzene concentrations in the product cumene. The use of such additional equipment or process modifications on a commercial scale would be highly expensive. Thus, in an effort to avoid such additional expenditure, the reason for the high amounts of ethylbenzene in the product was sought. It was surprisingly discovered that these undesirably high amounts of ethylbenzene are caused by the use of catalysts which contained low concentrations of ammonium ions, concentrations less than about 250 ppmw, calculated as $(NH_4)_2O$ on a volatiles-free basis. By providing the catalyst with an ammonium ion concentration higher than this minimum level, the amount of ethylbenzene contamination in the product cumene can be reduced to a value such that no further processing of the product cumene is necessary.

It will be understood that the flow scheme set forth in FIG. 1 can be used to produce ethylbenzene as a desired product by simply substituting ethylene for the propylene introduced into the process through line 10. When this is done, ethylbenzene instead of cumene is recovered overhead of distillation column 42 through line 44 and diethylbenzene and triethylbenzene are passed through lines 54 and 58 into transalkylation reactor 60 where they are converted via reaction with benzene into additional ethylbenzene product.

The nature and objects of the invention are further illustrated by the following example which is provided for illustrative purposes only and not to limit the invention as defined by the claims. The example demonstrates that the production of undesired by-products during transalkylation is minimized and therefore selectivity to the desired product is maximized if the catalyst contains greater than a residual amount of ammonium ions.

EXAMPLE

Three catalysts containing different concentrations of ammonium ions were prepared by mulling mixtures of the steam-stabilized, modified Y zeolite known as LZY-82 zeolite with Catapal alumina that had been peptized with nitric acid. The mulled mixtures were extruded through a clover leaf shaped die and dried overnight at 110° C. The dried extrudates were calcined in air under conditions such that the concentration of ammonium ions in Catalysts 1 and 3 was, respectively, 50 and 5800 ppmw, calculated as $(NH_4)_2O$ on a volatiles-free basis. Catalyst 2 was derived from Catalyst 3 by recalcining Catalyst 3 to lower its ammonium ion concentration from 5800 ppmw to 220 ppmw, calculated as $(NH_4)_2O$. Each of the three calcined catalysts contained 90 weight percent LZY-82 zeolite and 10 weight percent alumina. The ammonium ion concentration of each catalyst was separately determined by adding a ground sample of each catalyst to a caustic solution and distilling off as much ammonia as could be generated from each sample using a commercial ammonia-by-distillation apparatus (Tecator Kjeltec Distillation System Model 1030). The evolved ammonia was trapped in a boric acid solution which was titrated to determine the amount of ammonia evolved from each catalyst sample. The ammonium ion concentration of each catalyst was then calculated from this number.

The three catalysts prepared as described above were evaluated for selectivity in producing cumene by the transalkylation of benzene with diisopropylbenzene as described below. Ten grams of each catalyst were separately placed in the form of a fixed bed in a pilot plant size reactor vessel surrounded by a constant temperature fluidized sand bath to control the reactor temperature. A mixture of 91 weight percent reagent grade benzene and 9 weight percent reagent grade diisopropylbenzene isomers, primarily 1,4 diisopropylbenzene, was then passed downwardly through the catalyst bed at temperatures ranging between 305° F. and 365° F. and at a pressure of 500 p.s.i.g. The weight hourly space velocity was 2.4 reciprocal hours. The reactor temperature was varied between 305° F. and 365° F. to control conversion of the diisopropylbenzene. The liquid effluent from the reactor was collected for 12 hour periods and then analyzed by gas chromotography using a flame ionization detector. Typical concentration ranges of some of the compounds found in the reactor effluent over a wide range of conversions is set forth below in Table 1.

TABLE 1

Typical Product Yields

| Compound | Typical Yield Ranges (Mole Percent) |
| --- | --- |
| cumene | 6.0–8.0 |
| benzene | 90–92 |
| 1,3 diisopropylbenzene | 0.4–0.9 |
| 1,2 diisopropylbenzene | 0.002–0.006 |
| 1,4 diisopropylbenzene | 0.2–0.6 |
| 1,2,4 triisopropylbenzene | 0.003–0.001 |
| n-propylbenzene | 0.00–0.01 |
| ethylbenzene | 0.00–0.02 |
| 1,1 diphenylpropane | 0.005–0.010 |

As can be seen from Table 1, the yield of ethylbenzene is quite low compared to the desired cumene. However, the product cumene obtained via the process depicted in FIG. 1 may contain concentrations of ethylbenzene which may require, at substantial capital investment, additional equipment or process modifications to produce cumene at the desired purity level. Because of this, it is normally desirable that the yield of ethylbenzene in both the alkylation and transalkylation reactors be kept to a minimum. Thus, the performance of Catalysts 1 through 3 was evaluated by plotting in FIG. 2 the ethylbenzene concentration in the effluent from the above-described transalkylation reactor versus the diisopropylbenzene conversion. Each data point was obtained by averaging the measured compositions and calculated conversions over a several day period of steady state operation. The data in FIG. 2 indicate that low concentrations of ammonium ions in the catalyst tend to yield undesirably high concentrations of ethylbenzene, i.e., concentrations over 0.002 mole percent, even at diisopropylbenzene conversions below 80 percent where commercial operations normally take place.

Figure 2:
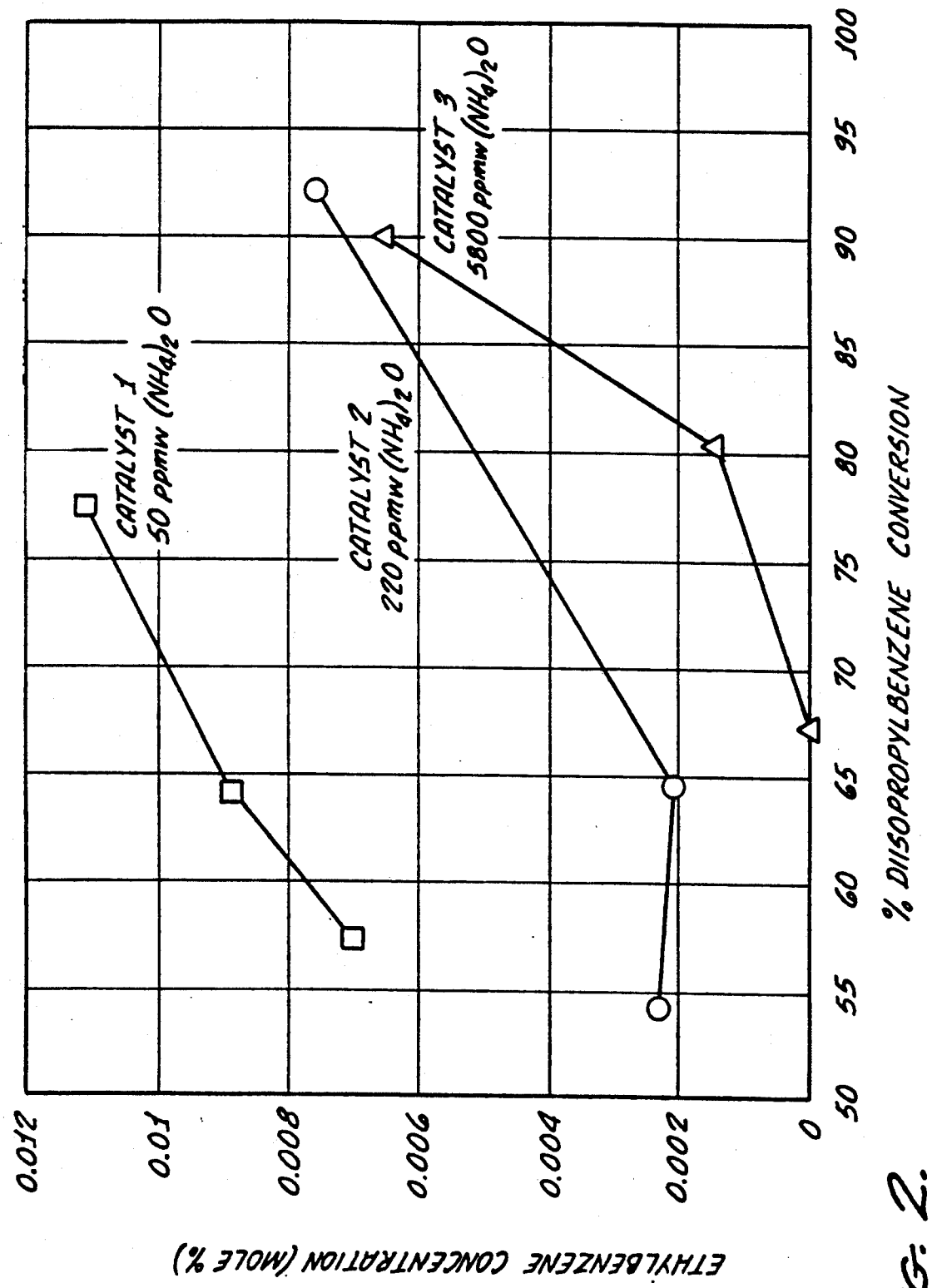
FIG. 2 is a plot which shows the concentration of undesirable ethylbenzene in the product resulting from the transalkylation of benzene with diisopropylbenzene to produce cumene versus the conversion of diisopropylbenzene at various concentrations of ammonium ions in the catalyst.
Figure 3:
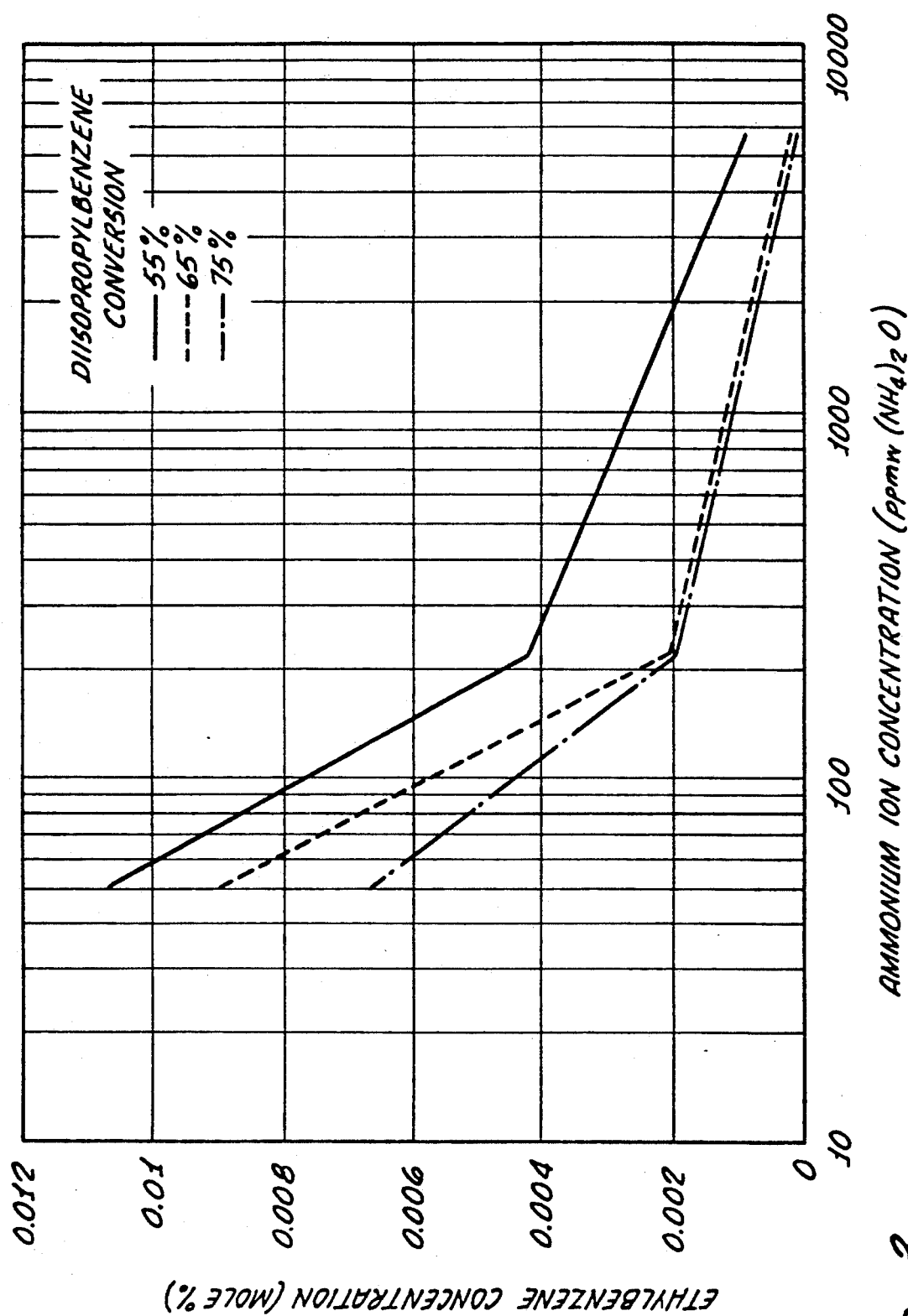
FIG. 3 is a plot derived from FIG. 2 which shows the concentration of undesirable ethylbenzene in the product resulting from the transalkylation of benzene with diisopropylbenzene to produce cumene versus the ammonium ion concentration in the catalyst at diisopropylbenzene conversions of 55, 65 and 75 percent.

To more clearly show the effect of ammonium ion concentration in the catalyst on selectivity, the data in FIG. 2 was replotted in FIG. 3 to show how the ethylbenzene concentration varied with changes in the ammonium ion concentration of the catalyst at diisopropylbenzene conversion levels of 55, 65 and 75 percent. These conversion levels are typical for commercial operations. As can be seen from FIG. 3, undesirably large amounts of ethylbenzene are obtained with catalysts which contain ammonium ion concentrations below about 250 ppmw, calculated as $(NH_4)_2O$ on a volatiles-free basis. The data indicate that, in order to maintain the concentration of undesirable ethylbenzene below 0.002 mole percent at diisopropylbenzene conversions below 75 percent, the catalyst should contain concentrations of ammonium ions greater than about 2000 ppmw. The data also show that catalysts containing greater than about 6000 ppmw ammonium ions will decrease the yield of undesirable ethyl-benzene to below 0.001 mole percent. Since a relatively high concentration of ammonium ions can deleteriously affect the activity of an alkylation catalyst, the effects on selectivity shown in FIG. 3 must be balanced against the effects on activity in order to determine the optimum concentration of ammonium ions. Typically, this concentration will range somewhere between 1000 and 18,000 ppmw, calculated as $(NH_4)_2O$ on a volatiles-free basis, preferably between about 2000 and about 15,000 ppmw, more preferably between about 3000 and about 10,000 ppmw, and most preferably between about 4000 and 8000 ppmw.

Although this invention has been primarily described in conjunction with an example and by reference to embodiments thereof, it is evident that many alternatives, modifications and variations will be apparent to those skilled in the art in light of the foregoing description. Accordingly, it is intended to embrace within the invention all such alternatives, modifications and variations that fall within the spirit and scope of the appended claims.

We claim:

1. A process for producing an alkylated organic compound via alkylation and/or transalkylation which comprises contacting an organic feedstock with an organic reactant in the presence of a catalyst under conditions such that components of said organic feedstock react with said organic reactant to form said alkylated compound, wherein said catalyst comprises a molecular sieve having alkylation and/or transalkylation activity and contains, after calcination, between about 250 and about 20,000 ppmw ammonium ions, calculated as $(NH_4)_2O$ on a volatiles-free basis.

2. A process as defined by claim 1 wherein said alkylated organic compound is produced via alkylation, said organic feedstock comprises an aromatic compound and said organic reactant comprises an olefin.

3. A process as defined by claim 2 wherein said alkylated organic compound comprises cumene, said aromatic compound comprises benzene and said olefin comprises propylene.

4. A process as defined by claim 2 wherein said alkylated organic compound comprises ethylbenzene, said aromatic compound comprises benzene and said olefin comprises ethylene.

5. A process as defined by claim 1 wherein said catalyst further comprises an inorganic refractory oxide.

6. A process as defined by claim 5 wherein said molecular sieve is a steam-stabilized Y zeolite.

7. A process as defined by claim 6 wherein said catalyst contains, after calcination, between about 2,000 and 8,000 ppmw ammonium ions, calculated as $(NH_4)_2O$ on a volatiles-free basis.

8. A process as defined by claim 7 wherein said inorganic refractory oxide is alumina.

9. A process as defined by claim 5 wherein said molecular sieve has an overall silica-to-alumina mole ratio between 5.0 and 20.

10. A process for alkylating an aromatic compound to form an alkylated aromatic which comprises contacting said aromatic compound with an alkylating agent under alkylation conditions in the presence of a catalyst comprising (1) a zeolitic molecular sieve having alkylation activity and (2) an inorganic refractory oxide, said catalyst being devoid of hydrogenation metal components and containing, after calcination, between about 250 and about 20,000 ppmw ammonium ions, calculated as $(NH_4)_2O$ on a volatiles-free basis.

11. A process as defined by claim 10 wherein said aromatic compound is selected from the group consisting of monocyclic aromatic compounds, polycyclic aromatic compounds, and substituted derivatives thereof.

12. A process as defined by claim 11 wherein said aromatic compound comprises benzene.

13. A process as defined by claim 12 wherein said alkylating agent comprises a $C_2-C_{25}$ olefin.

14. A process as defined by claim 13 wherein said alkylating agent comprises ethylene or propylene.

15. A process as defined by claim 10 wherein said zeolitic molecular sieve is LZY-82 zeolite.

16. A process as defined by claim 10 wherein said zeolitic molecular sieve is a steam-stabilized Y zeolite, said catalyst contains, after calcination, between about 2,000 and 8,000 ppmw ammonium ions, calculated as $(NH_4)_2O$ on a volatiles-free basis, and said inorganic refractory oxide is alumina.

17. A process as defined by claim 10 wherein said zeolitic molecular sieve has a Constraint Index below about 1.0.

18. A process for the transalkylation of an aromatic compound which comprises contacting said aromatic compound with a transalkylation agent under transalkylation conditions in the presence of a catalyst comprising (1) a zeolitic molecular sieve having transalkylation activity, and (2) an inorganic refractory oxide, said catalyst being substantially devoid of hydrogenation metal components and containing, after calcination, between about 250 and about 20,000 ppmw ammonium ions, calculated as $(NH_4)_2O$ on a volatiles-free basis.

19. A process as defined by claim 18 wherein said aromatic compound comprises benzene and said transalkylation agent comprises diisopropylbenzene.

20. A process as defined by claim 18 wherein said aromatic compound comprises benzene and said transalkylation agent comprises diethylbenzene.

21. A process as defined by claim 18 wherein said zeolitic molecular sieve is LZY-82 zeolite.

22. A process as defined by claim 18 wherein said zeolitic molecular sieve is a steam-stabilized Y zeolite, said catalyst contains, after calcination, between about 2,000 and 8,000 ppmw ammonium ions, calculated as $(NH_4)_2O$ on a volatiles-free basis, and said inorganic refractory oxide is alumina.

23. A process for making a monoalkylated aromatic compound which comprises:
 (a) contacting an aromatic compound with an alkylating agent in an alkylation zone under alkylation conditions in the presence of a catalyst comprising, after calcination, a modified Y zeolite having alkylation activity, an inorganic refractory oxide and between about 250 and about 20,000 ppmw ammonium ions, calculated as $(NH_4)_2O$ on a volatiles-free basis, to produce an effluent containing polyalkylated aromatic compounds, an unconverted aromatic compound, and said monoalkylated aromatic compound, wherein said modified Y zeolite is selected from the group consisting of ultrastable Y zeolites, steam-stabilized Y zeolites and dealuminated Y zeolites;
 (b) recovering in a first separation zone said uncoverted aromatic compound from the effluent of said alkylation zone and recycling a first portion of said recovered unconverted aromatic compound to said alkylation zone;
 (c) recovering in a second separation zone said monoalkylated aromatic compound from the effluent of said first separation zone;
 (d) recovering in a third separation zone at least a portion of said polyalkylated aromatic compounds from the effluent of said second separation zone;
 (e) contacting in a transalkylation zone said polyalkylated aromatic compounds recovered from the effluent of said second separation zone with a second portion of said unconverted aromatic compound recovered from said first separation zone under transalkylation conditions in the presence of a catalyst comprising, after calcination, a modified Y zeolite having transalkylation activity, an inorganic refractory oxide and between about 250 and about 20,000 ppmw ammonium ions, calculated as $(NH_4)_2O$ on a volatiles-free basis, to produce an effluent containing said monoalkylated aromatic compound, wherein said modified Y zeolite is selected from the group consisting of ultrastable Y zeolites, steam-stabilized Y zeolites and dealuminated Y zeolites; and
 (f) recycling the effluent from said transalkylation zone to said first separation zone.

24. A process as defined by claim 23 wherein said monoalkylated aromatic compound in step (a) comprises cumene, said aromatic compound comprises benzene and said alkylating agent comprises propylene.

25. A process as defined by claim 23 wherein said monoalkylated aromatic compound in step (a) comprises ethylbenzene, said aromatic compound comprises benzene and said alkylating agent comprises ethylene.

26. A process as defined by claim 23 wherein said catalyst in said alkylation zone and said catalyst in said transalkylation zone each contain, after calcination, between about 2,000 and 8,000 ppmw ammonium ions, calculated as $(NH_4)_2Z_2O$ on a volatiles-free basis, and the inorganic refractory oxide in each of said catalysts is alumina.

27. A process for the acid catalyzed chemical conversion of a feedstock containing organic compounds into reaction products which comprises contacting said feedstock under acid catalyzed conversion conditions with a catalyst comprising a molecular sieve having catalytic activity, said catalyst containing, after calcination, between about 250 and about 20,000 ppmw ammonium ions, calculated as $(NH_4)_2O$ on a volatiles-free basis.

28. A process as defined by claim 27 wherein said acid catalyzed chemical conversion process is selected from the group consisting of alkylation, transalkylation, isomerization and disproportionation.

29. A process as defined by claim 28 wherein said molecular sieve is a steam-stabilized Y zeolite, said catalyst contains, after calcination, greater than about 2,000 ppmw ammonium ions, calculated as $(NH_4)_2O$ on a volatiles-free basis, and said catalyst further comprises an inorganic refractory oxide.

30. A process as defined by claim 29 wherein the concentration of ammonium ions in said catalyst after calcination is between about 3000 and 8,000 ppmw, calculated as $(NH_4)_2O$ on a volatiles-free basis, and said inorganic refractory oxide is alumina.

31. A process as defined by claim 27 wherein said molecular sieve has a Constraint Index below about 1.0.

* * * * *

UNITED STATES PATENT AND TRADEMARK OFFICE
CERTIFICATE OF CORRECTION

PATENT NO. : 5,157,180

DATED : October 20, 1992

INVENTOR(S) : West et al.

It is certified that error appears in the above-identified patent and that said Letters Patent is hereby corrected as shown below:

On title page, column 1, item [56], line 5 under "U.S. PATENT DOCUMENTS", delete "3,641,117" and insert -- 3,641,177 --.

Column 14, claim 26, line 49, delete "$(NH_4)Z_2O$" and insert -- $(NH_4)_2O$ --.

Signed and Sealed this

Twenty-ninth Day of March, 1994

Attest:

BRUCE LEHMAN

*Attesting Officer*  *Commissioner of Patents and Trademarks*